(12) United States Patent
Dorian et al.

(10) Patent No.: US 11,534,533 B2
(45) Date of Patent: Dec. 27, 2022

(54) APPARATUS AND METHODS FOR PROCESSING BLOOD

(71) Applicant: Hanuman Pelican, Inc., New Orleans, LA (US)

(72) Inventors: Randy Dorian, San Diego, CA (US); Michael D. Leach, Warsaw, IN (US); Richard W. Storrs, Berkeley, CA (US); Scott R. King, New Orleans, LA (US)

(73) Assignee: Hanuman Pelican, Inc., New Orleans, LA (US)

( * ) Notice: Subject to any disclaimer, the term of this patent is extended or adjusted under 35 U.S.C. 154(b) by 0 days.

(21) Appl. No.: 16/450,669

(22) Filed: Jun. 24, 2019

(65) Prior Publication Data
US 2020/0009304 A1 Jan. 9, 2020

Related U.S. Application Data

(60) Provisional application No. 62/695,649, filed on Jul. 9, 2018.

(51) Int. Cl.
*A61M 1/02* (2006.01)
*A61M 1/36* (2006.01)
(Continued)

(52) U.S. Cl.
CPC ........ *A61M 1/0272* (2013.01); *A61M 1/0259* (2013.01); *A61M 1/3693* (2013.01);
(Continued)

(58) Field of Classification Search
CPC .............. A61M 1/0272; A61M 1/0259; A61M 1/3693; A61M 1/029; G01N 33/491;
(Continued)

(56) References Cited

U.S. PATENT DOCUMENTS 3,586,064 A * 6/1971 Brown .................... B01L 3/502
141/1
3,914,985 A  10/1975 von Behrens
(Continued)

FOREIGN PATENT DOCUMENTS

EP  0385953  9/1990
EP  0778944  6/1997
(Continued)

OTHER PUBLICATIONS

Rohrer, Device for receiving liquids and for exactly removing single phases of the received liquid, Jul. 4, 2018, https://patents.google.com/patent/EP3342436B1/en?oq=EP+3342436 (Year: 2018).*

*Primary Examiner* — Nam X Nguyen
*Assistant Examiner* — Ekandra S. Miller-Cruz
(74) *Attorney, Agent, or Firm* — Levine Bagade Han LLP

(57) ABSTRACT

Apparatus and methods for processing blood are disclosed in which one variation generally comprises a tube defining a channel and an access tube extending into the channel. An open cell matrix configured to entrap red blood cells may be positioned within at least a portion of the channel. Another variation generally comprises a cylindrical tube and a plunger slidably positioned within the channel. The plunger also has a funnel positioned upon the plunger and is movable therewith. Both the plunger and funnel define a fluid channel through and in communication with the cylindrical tube.

6 Claims, 7 Drawing Sheets

(51) Int. Cl.
  *G01N 33/49* (2006.01)
  *G01N 1/40* (2006.01)
  *B01L 3/00* (2006.01)

(52) U.S. Cl.
  CPC ........... *G01N 33/491* (2013.01); *A61M 1/029* (2013.01); *B01L 3/5021* (2013.01); *B01L 2400/0478* (2013.01); *G01N 2001/4083* (2013.01)

(58) Field of Classification Search
  CPC ..... G01N 2001/4083; B01L 2400/0478; B01L 3/5021
  USPC ...................................................... 210/782
  See application file for complete search history.

(56) References Cited

U.S. PATENT DOCUMENTS

| | | | |
|---|---|---|---|
| 3,960,727 A * | 6/1976 | Hochstrasser | B01D 33/01 210/782 |
| 4,021,352 A * | 5/1977 | Sarstedt | B01D 33/01 210/359 |
| 4,152,270 A | 5/1979 | Cornell | |
| 4,210,623 A | 7/1980 | Breno et al. | |
| 4,417,981 A * | 11/1983 | Nugent | G01N 33/491 210/209 |
| 4,867,887 A | 9/1989 | Smith | |
| 5,064,541 A * | 11/1991 | Jeng | B01D 39/2075 210/767 |
| 5,550,060 A | 8/1996 | Saunders et al. | |
| 5,585,007 A * | 12/1996 | Antanavich | A61L 24/106 210/500.38 |
| 5,707,876 A | 1/1998 | Levine | |
| 5,860,937 A * | 1/1999 | Cohen | B01L 3/50215 600/576 |
| 6,123,655 A | 9/2000 | Fell | |
| 6,221,655 B1 * | 4/2001 | Fung | B01L 3/5021 422/504 |
| 6,465,256 B1 | 10/2002 | Iskra | |
| 6,506,167 B1 | 1/2003 | Ishimoto et al. | |
| 7,001,774 B1 * | 2/2006 | Gamble | G01N 1/38 436/180 |
| 7,074,577 B2 | 7/2006 | Haubert et al. | |
| 7,077,273 B2 | 7/2006 | Ellsworth et al. | |
| 7,153,477 B2 | 12/2006 | DiCesare et al. | |
| 7,179,391 B2 | 2/2007 | Leach et al. | |
| 7,223,346 B2 | 5/2007 | Dorian et al. | |
| 7,329,534 B2 | 2/2008 | Haubert et al. | |
| 7,358,095 B2 | 4/2008 | Haubert et al. | |
| 7,374,678 B2 | 5/2008 | Leach et al. | |
| 7,445,125 B2 | 11/2008 | Ellsworth et al. | |
| 7,470,371 B2 | 12/2008 | Dorian et al. | |
| 7,771,590 B2 | 8/2010 | Leach et al. | |
| 7,780,860 B2 | 8/2010 | Higgins et al. | |
| 7,798,021 B2 | 9/2010 | Gamble et al. | |
| 7,845,499 B2 | 12/2010 | Higgins et al. | |
| 7,947,236 B2 | 5/2011 | Losada et al. | |
| 7,976,796 B1 * | 7/2011 | Smith | B01L 3/5021 494/67 |
| 7,992,725 B2 | 8/2011 | Leach et al. | |
| 8,012,742 B2 | 9/2011 | Haubert et al. | |
| 8,048,297 B2 | 11/2011 | Leach et al. | |
| 8,048,321 B2 | 11/2011 | Leach et al. | |
| 8,119,013 B2 | 2/2012 | Leach et al. | |
| 8,177,072 B2 | 5/2012 | Chapman et al. | |
| 8,187,477 B2 | 5/2012 | Dorian et al. | |
| 8,236,258 B2 | 8/2012 | Leach et al. | |
| 8,313,954 B2 | 11/2012 | Leach et al. | |
| 8,328,024 B2 | 12/2012 | Leach et al. | |
| 8,348,066 B2 | 1/2013 | Ellsworth | |
| 8,377,395 B2 | 2/2013 | Coleman | |
| 8,394,342 B2 | 3/2013 | Felix et al. | |
| 8,445,264 B2 | 5/2013 | Seubert et al. | |
| 8,474,630 B2 | 7/2013 | Dorian et al. | |
| 8,506,823 B2 | 8/2013 | Chapman et al. | |
| 8,511,479 B2 | 8/2013 | Chapman et al. | |
| 8,511,480 B2 | 8/2013 | Chapman et al. | |
| 8,518,272 B2 | 8/2013 | Hoeppner | |
| 8,596,470 B2 | 12/2013 | Leach et al. | |
| 8,603,345 B2 | 12/2013 | Ross et al. | |
| 8,603,346 B2 | 12/2013 | Leach et al. | |
| 8,632,736 B2 | 1/2014 | Spatafore et al. | |
| 8,632,740 B2 | 1/2014 | Dastane et al. | |
| 8,747,781 B2 | 6/2014 | Bartfield et al. | |
| 8,794,452 B2 | 8/2014 | Crawford et al. | |
| 8,808,551 B2 | 8/2014 | Leach et al. | |
| 8,950,586 B2 | 2/2015 | Dorian et al. | |
| 8,992,862 B2 | 3/2015 | Leach et al. | |
| 8,998,000 B2 | 4/2015 | Crawford et al. | |
| 9,011,800 B2 | 4/2015 | Leach et al. | |
| 9,079,123 B2 | 7/2015 | Crawford et al. | |
| 9,114,334 B2 | 8/2015 | Leach et al. | |
| 9,120,095 B2 | 9/2015 | O'Connel, Jr. | |
| 9,138,664 B2 | 9/2015 | Leach et al. | |
| 9,162,232 B2 | 10/2015 | Ellsworth | |
| 9,239,276 B2 | 1/2016 | Landrigan et al. | |
| 9,272,083 B2 | 3/2016 | Duffy et al. | |
| 9,333,445 B2 | 5/2016 | Battles et al. | |
| 9,339,741 B2 | 5/2016 | Newby et al. | |
| 9,364,828 B2 | 6/2016 | Crawford et al. | |
| 9,375,661 B2 | 6/2016 | Chapman et al. | |
| 9,393,575 B2 | 7/2016 | Ellsworth et al. | |
| 9,393,576 B2 | 7/2016 | Ellsworth et al. | |
| 9,399,226 B2 | 7/2016 | Ellsworth et al. | |
| 9,452,427 B2 | 9/2016 | Felix et al. | |
| 9,642,956 B2 | 5/2017 | Landrigan et al. | |
| 9,649,579 B2 | 5/2017 | Leach et al. | |
| 9,656,274 B2 | 5/2017 | Ellsworth et al. | |
| 9,694,359 B2 | 7/2017 | Losada et al. | |
| 9,700,886 B2 | 7/2017 | Felix et al. | |
| 9,714,890 B2 | 7/2017 | Newby et al. | |
| 9,731,290 B2 | 8/2017 | Crawford et al. | |
| 9,802,189 B2 | 10/2017 | Crawford et al. | |
| 9,897,589 B2 | 2/2018 | Woodell-May | |
| 9,919,307 B2 | 3/2018 | Crawford et al. | |
| 9,919,308 B2 | 3/2018 | Crawford et al. | |
| 9,919,309 B2 | 3/2018 | Crawford et al. | |
| 9,933,344 B2 | 4/2018 | Newby et al. | |
| 9,937,445 B2 | 4/2018 | King et al. | |
| 10,005,081 B2 | 6/2018 | Duffy et al. | |
| 10,183,042 B2 | 1/2019 | Leach et al. | |
| 10,343,157 B2 | 7/2019 | Crawford et al. | |
| 10,350,591 B2 | 7/2019 | Felix et al. | |
| 10,376,879 B2 | 8/2019 | Crawford et al. | |
| 10,393,728 B2 | 8/2019 | Woodell-May | |
| 10,413,898 B2 | 9/2019 | Crawford et al. | |
| 10,456,782 B2 | 10/2019 | Crawford et al. | |
| 10,603,665 B2 | 3/2020 | Levine et al. | |
| 10,618,044 B1 | 4/2020 | Petrie, Jr. | |
| 2005/0109716 A1 * | 5/2005 | Leach | B01L 3/502 210/787 |
| 2005/0139547 A1 | 6/2005 | Manoussakis et al. | |
| 2009/0050553 A1 * | 2/2009 | Okamoto | B01L 3/5635 210/233 |
| 2010/0256595 A1 | 10/2010 | Leach et al. | |
| 2011/0281714 A1 | 11/2011 | Dorian et al. | |
| 2012/0053041 A1 | 3/2012 | Ihm et al. | |
| 2012/0129676 A1 | 5/2012 | Duffy et al. | |
| 2014/0042094 A1 | 2/2014 | Montagu et al. | |
| 2015/0231626 A1 | 8/2015 | Shi et al. | |
| 2015/0367064 A1 * | 12/2015 | Pennie | B01L 3/50215 494/37 |
| 2016/0030661 A1 | 2/2016 | Hwang | |
| 2016/0279551 A1 * | 9/2016 | Foucault | A61M 1/81 |
| 2016/0367982 A1 * | 12/2016 | Pennie | B01L 3/5021 |
| 2017/0304823 A1 | 10/2017 | Sparks et al. | |
| 2018/0304251 A1 | 10/2018 | Ellson et al. | |
| 2018/0353952 A1 | 12/2018 | Olson | |
| 2020/0009551 A1 | 1/2020 | Dorian et al. | |
| 2020/0009552 A1 | 1/2020 | Crawford et al. | |
| 2020/0129560 A1 | 4/2020 | Centeno et al. | |
| 2020/0197929 A1 | 6/2020 | Weinstock et al. | |

(56) References Cited

U.S. PATENT DOCUMENTS

| | | |
|---|---|---|
| 2020/0215243 A1 | 7/2020 | Dorian et al. |
| 2020/0246516 A1 | 8/2020 | Dorian et al. |
| 2020/0289720 A1 | 9/2020 | Streit |

FOREIGN PATENT DOCUMENTS

| | | |
|---|---|---|
| EP | 3342436 | 7/2018 |
| WO | WO 2007/000966 | 1/2007 |
| WO | WO 2010/138895 | 12/2010 |
| WO | WO 2014/120797 | 8/2014 |
| WO | WO 2016/205640 | 12/2016 |
| WO | WO 2018/197562 | 11/2018 |
| WO | WO 2018/197564 | 11/2018 |
| WO | WO 2018/197592 | 11/2018 |
| WO | WO 2020/013981 | 1/2020 |
| WO | WO 2020/013997 | 1/2020 |
| WO | WO 2020/154305 | 7/2020 |
| WO | WO 2020/163105 | 8/2020 |

* cited by examiner

APPARATUS AND METHODS FOR PROCESSING BLOOD

CROSS-REFERENCE TO RELATED APPLICATIONS

This application claims the benefit of priority to U.S. Prov. 62/695,649 filed Jul. 9, 2018, which is incorporated herein by reference in its entirety.

FIELD OF THE INVENTION

The present invention relates to apparatus and methods for separating blood components. More particularly, the present invention relates to apparatus and methods for effectively separating and removing specific components from blood.

BACKGROUND OF THE INVENTION

Blood may be fractionated and the different fractions of the blood used for different medical needs. For instance, anemia (low erythrocyte levels) may be treated with infusions of erythrocytes. Thrombocytopenia (low thrombocyte (platelet) levels) may be treated with infusions of platelet concentrate.

The sedimentation of the various blood cells and plasma is based on the different specific gravity of the cells and the viscosity of the medium. When sedimented to equilibrium, the component with the highest specific gravity (density) eventually sediments to the bottom, and the lightest rises to the top. Under the influence of gravity or centrifugal force, blood spontaneously sediments into three layers. At equilibrium the top, low-density layer is a straw-colored clear fluid called plasma. Plasma is a water solution of salts, metabolites, peptides, and many proteins ranging from small (insulin) to very large (complement components). Plasma per se has limited use in medicine but may be further fractionated to yield proteins used, for instance, to treat hemophilia (factor VIII) or as a hemostatic agent (fibrinogen). The term platelet rich plasma (PRP) is used for this component because most of the plasma proteins and platelets in the whole blood are in the plasma following slow centrifugation so the concentration of platelets in the plasma has increased while suspended in supernatant plasma. The uppermost layer after centrifugation typically contains plasma proteins only and is typically called platelet-poor plasma (PPP) due to the absence or low number of platelets as a result of a "hard spin".

The bottom, high-density layer is a deep red viscous fluid comprising nuclear red blood cells (RBC) specialized for oxygen transport. The red color is imparted by a high concentration of chelated iron or heme that is responsible for the erythrocytes high specific gravity. Packed erythrocytes, matched for blood type, are useful for treatment of anemia caused by, e.g., bleeding. The relative volume of whole blood that consists of erythrocytes is called the hematocrit, and in normal human beings can range from about 38% to about 54%.

The intermediate layer is the smallest layer, appearing as a thin white band on top the erythrocyte layer and below the plasma, and is called the buffy coat. The buffy coat itself has two major components, nucleated leukocytes (white blood cells) and anuclear smaller bodies called platelets (or thrombocytes). Leukocytes confer immunity and contribute to debris scavenging. Platelets seal ruptures in the blood vessels to stop bleeding and deliver growth and wound healing factors to the wound site. The buffy coat may be separated from whole blood when the blood is subjected to a "hard spin" in which the whole blood is spun hard enough and long enough so that platelets sediment from plasma onto packed red cells and white cells percolate up through red cell pack to the interface between red cells and plasma.

When whole blood is centrifuged at a low speed (e.g., up to 1,000 g) for a short time (e.g., two to four minutes) white cells sediment faster than red cells and both sediment much faster than platelets. At higher speeds the same distribution is obtained in a shorter time. The method of harvesting PRP from whole blood is based on this principle. Centrifugal sedimentation that takes the fractionation only as far as separation into packed erythrocytes and PRP is called a "soft spin" which is typically used to describe centrifugation conditions under which erythrocytes are sedimented but platelets remain in suspension. "Hard spin" is typically used to describe centrifugation conditions under which erythrocytes sediment and platelets sediment in a layer immediately above the layer of erythrocytes.

The auto-transfusion equipment used to make autologous platelet concentrates requires a skilled operator and considerable time and expense and these devices require a large prime volume of blood. While many of these devices have somewhat reduced the cost and the time required, skilled operators and time are still required. Accordingly, there remains a need for simple and effective methods and devices for separating and removing components from whole blood.

SUMMARY OF THE INVENTION

The present invention relates to apparatus and methods for rapid fractionation of blood into its different components, e.g., erythrocyte, plasma, and platelet fractions. The devices and methods described have particular value for rapid preparation of autologous concentrated platelet fractions, e.g., to help or speed healing.

In separating out the fractional layers from blood, one variation may include a centrifuge tube fitted with an access tube extending within and having a predefined length for withdrawing the fractional layers. A centrifuge tube may include an access tube extending within the channel of the tube from a cover or seal. The access tube may be fluidly coupled to a septum luer through which a line or syringe may be attached. In one variation, the access tube length may be about half of the centrifuge tube length so that the opening of the access tube may be suitably positioned to withdraw specified fractional layers of the separated blood. In one example, whole blood may be received within the centrifuge tube and sealed with the access tube extending within the blood. Alternatively, the blood may be introduced into the tube directly through the access tube and the tube may be subsequently sealed. Anticoagulants may be pre-loaded within the centrifuge tube or introduced into the tube along with the blood.

The centrifuge tube may be then subjected to a centrifuge or left to separate under the force of gravity. The resulting fractional layers will form within the tube with the RBC layer formed in the lower portion of centrifuge tube. The PRP layer will remain suspended above the sedimented RBC layer and with the length of the access tube properly sized, the opening will remain within the PRP layer. The blood cell-free PRP layer can then be recovered by withdrawal back into the syringe via the access tube. The process time can be reduced dramatically by briefly spinning the anticoagulated blood to pellet the blood cells.

If desired, an optional layer of a matrix, such as open cell foam, fabric mat, or other open matrix, can occupy the lower portion of the tube to entrap the sedimented blood cells and reduce the risk of disturbing the settled cells during handling.

In yet another variation, a cylindrical tube may have a closed floor and a plunger having a funnel attached. A plunger opening may be defined through the plunger and a length of tubing having an opening may be connected to the apex of the funnel. Rather than having a plunger pushed through the channel of the tube from an end opposite of where the fractional layer is removed, the plunger and funnel may be used to remove the fractional layer from the same end of where the plunger is actuated. In this manner, the plunger is pushed down into the tube and towards the floor rather than from the bottom of the tube away from the floor.

One variation of a method for separating blood into its fractional layers and then withdrawing specific layers using the tube may have the plunger and attached funnel initially positioned at the closed floor of the tube. The tubing may be seen extend from the funnel through the tube and terminating at the opening positioned externally of the tube. A syringe containing a volume of blood, e.g., anticoagulated blood, may be connected to the opening and then injected through the tubing, into the funnel, through the plunger, and into the tube which may force the plunger and funnel away from the floor as the blood enters the tube.

Once the tube has been sufficiently filled with the blood, the tubing may be detached from the top of the funnel which may be secured with a cap or seal in preparation for centrifugation with the funnel remaining in place upon the plunger. Once the tube and blood has been sufficiently centrifuged, the blood may have fractionalized into its component layers, e.g., a first PRP layer and a second RBC layer.

A tubing connected to a withdrawal syringe may be coupled to the funnel and the syringe may be used to draw the PRP layer directly through the funnel and into the syringe. Due to the vacuum drawn via the withdrawal syringe, the plunger and funnel may be forced to move further into the tube and towards the floor as the PRP layer is removed from the tube.

During withdrawal, because the plunger and funnel are moving into the PRP layer for collection, the platelets within the layer are no longer dragged against the walls of the tubing. Moreover, because the PRP layer (buffy coat, RBC layer) remains undisturbed until contacted with the funnel, the yield on platelets and white blood cells are potentially improved while contamination from the RBC layer is potentially reduced.

One variation of a separation apparatus generally comprises a tube having a first length and defining a channel within, an access tube having a second length and extending into the channel, and an open cell matrix configured to entrap red blood cells and positioned within at least a portion of the channel, wherein the access tube defines an opening which is positioned within proximity of the open cell matrix within the channel.

Another variation of a separation apparatus generally comprises a cylindrical tube defining an opening and a channel extending therethrough, a plunger defining a plunger fluid opening and slidably positioned within the channel, and a funnel positioned upon the plunger and movable therewith, wherein the funnel defines a funnel fluid opening in fluid communication with the plunger fluid opening.

One variation for a method of separating components from blood generally comprises introducing a volume of blood through a funnel and a plunger and into a channel defined by a cylindrical tube such that the funnel and plunger are moved from a first position within the tube to a second position in proximity to an opening defined by the tube, applying a centrifugal force to the volume of blood contained within the tube such that the blood forms at least a first fractional layer and a second fractional layer, and withdrawing at least the first fractional layer from the tube via the funnel and the plunger such that the funnel and plunger are moved from the second position back towards the first position.

DETAILED DESCRIPTION OF THE INVENTION

Throughout the description, terms such as "top", "above, "bottom", "below" are used to provide context with respect to the relative positioning of components when, e.g., a container tube with fractional components of blood are positioned when the longitudinal axis of a container tube is positioned upright or non-horizontally. Such description is used for illustrative purposes only.

As discussed herein, when sedimented to equilibrium, the component with the highest specific gravity (density) eventually sediments to the bottom, and the lightest rises to the top. Under the influence of gravity or centrifugal force, blood spontaneously sediments into three layers. At equilibrium the top, low-density layer is a straw-colored clear fluid called plasma. The term platelet rich plasma (PRP) is used for this component because most of the plasma proteins and platelets in the whole blood are in the plasma following slow centrifugation so the concentration of platelets in the plasma has increased while suspended in supernatant plasma. The bottom, high-density layer comprises sedimented red blood cells (RBC). The intermediate layer, if the blood is subjected to further centrifugation, is called the buffy coat.

SEDIMENTATION MATRIX

In separating out the fractional layers from blood, one variation may include a centrifuge tube fitted with an access tube extending within and having a predefined length for withdrawing the fractional layers. Because blood typically contains about 40% to 45% of red blood cells by volume, the resulting volume of the RBC layer after centrifugation can be determined relative to the height of the centrifugation tube.

Figure 1:
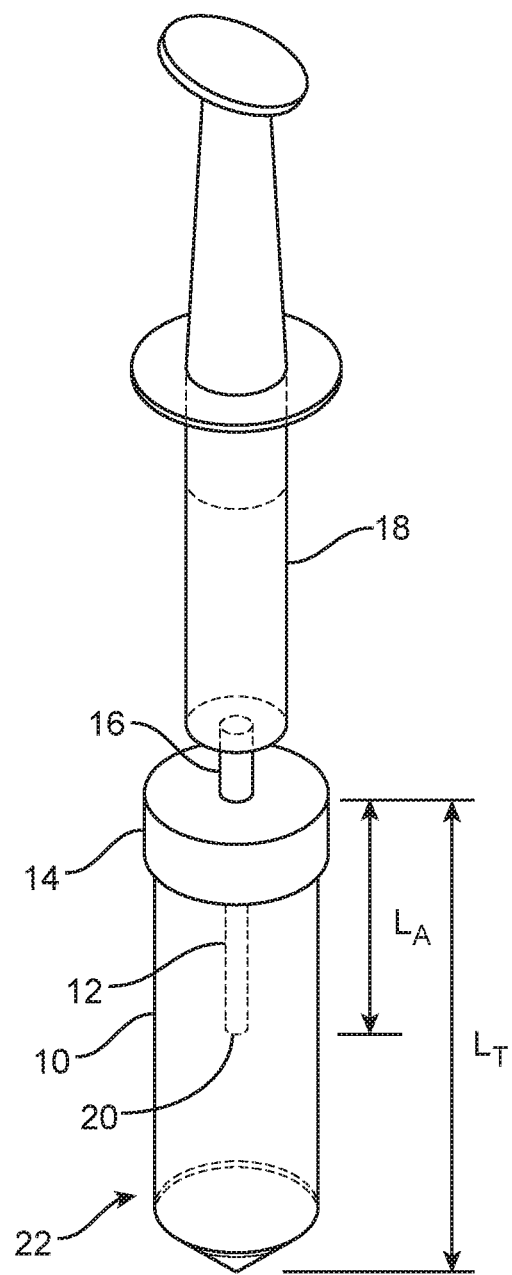
FIG. 1 shows a perspective view of one variation of a separation assembly having an access tube extending at least partially into the centrifuge tube.

FIG. 1 shows a variation in which the centrifuge tube 10 may include an access tube 12 extending within the channel of the tube 10 from a cover or seal 14. The access tube 12 may be fluidly coupled to a septum Luer 16 through which a line or syringe 18 may be attached. The access tube 12 may have a predefined access tube length $L_A$ which is less than the centrifuge tube length $L_T$, as shown. In one variation, the access tube length $L_A$ may be about half of the centrifuge tube length $L_T$. In other variations, the access tube length $L_A$ may range between, e.g., 30 to 50% of the centrifuge tube length $L_T$.

With the opening 20 of the access tube 12 positioned approximately half-way down the length of the centrifuge tube 10, the opening 20 may be suitably positioned to withdraw specified fractional layers of the separated blood. In one example, whole blood may be received within the centrifuge tube 10 and sealed with the access tube 12 extending within the blood. Alternatively, the blood may be introduced into the tube 10 directly through the access tube 12 and the tube may be subsequently sealed. Anticoagulants may be preloaded within the centrifuge tube 10 or introduced into the tube 10 along with the blood.

The centrifuge tube 10 may be then subjected to a centrifuge or left to separate under the force of gravity. The resulting fractional layers will form within the tube 10 with the RBC layer formed in the lower portion of centrifuge tube 22. The PRP layer will remain suspended above the sedimented RBC layer and with the length of the access tube 12 properly sized, the opening 20 will remain within the PRP layer. The blood cell-free PRP layer can then be recovered by withdrawal back into the syringe 18 via the access tube 12. The process time can be reduced dramatically by briefly spinning the anticoagulated blood to pellet the blood cells.

Figure 2A:
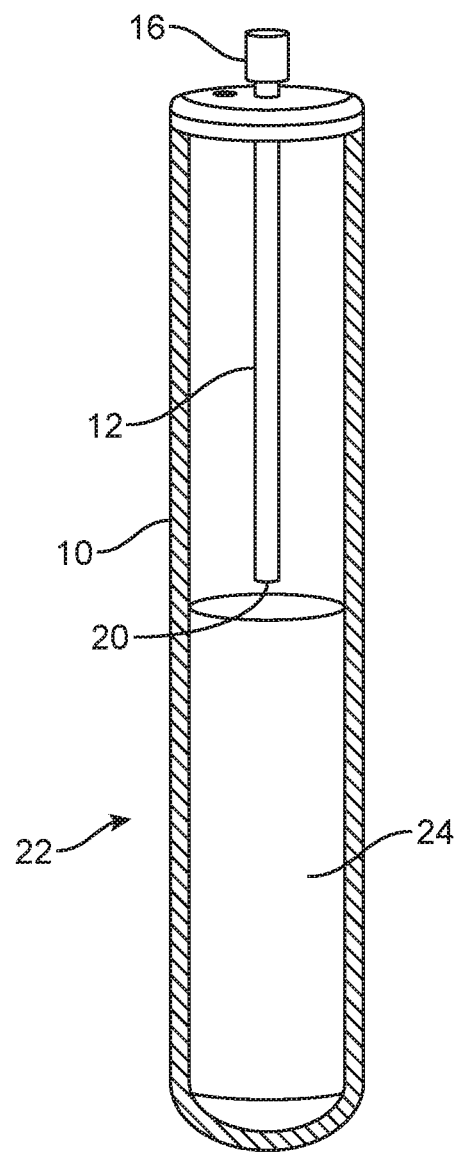
FIG. 2A shows a perspective view of another variation of the separation assembly having an access tube and a matrix for retaining specific blood components.

If desired, an optional layer of a matrix 24, such as open cell foam, fabric mat, or other open matrix, can occupy the lower portion 22 of the tube 10 to entrap the sedimented blood cells and reduce the risk of disturbing the settled cells during handling. FIG. 2A shows a perspective view of a tube 10 having the access tube 12 extending within to about half the length of the tube 10 such that the opening 20 is positioned above the matrix 24. The matrix 24 is shown as an open cell foam having defined pores which are large enough so that the red blood cells and white blood cells can penetrate into and become entrapped within the matrix 24 when the tube 10 is centrifuged. The PRP layer may remain suspended in the plasma fraction above the entrapped RBC layer for subsequent withdrawal through the access tube 12.

Figure 2B:
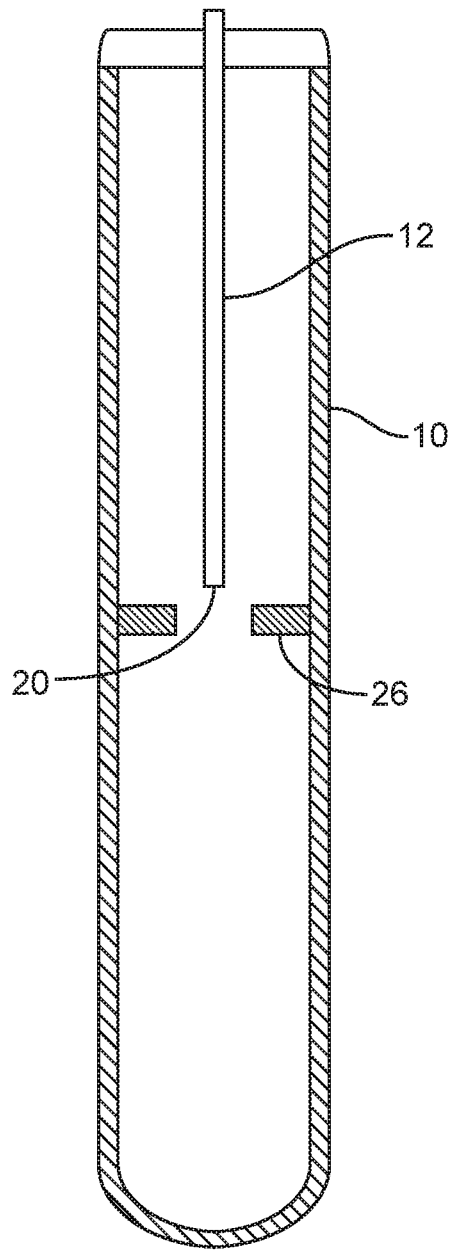
FIGS. 2B and 2C show side views of additional variations of the separation assembly having a matrix contained within.
Figure 2C:
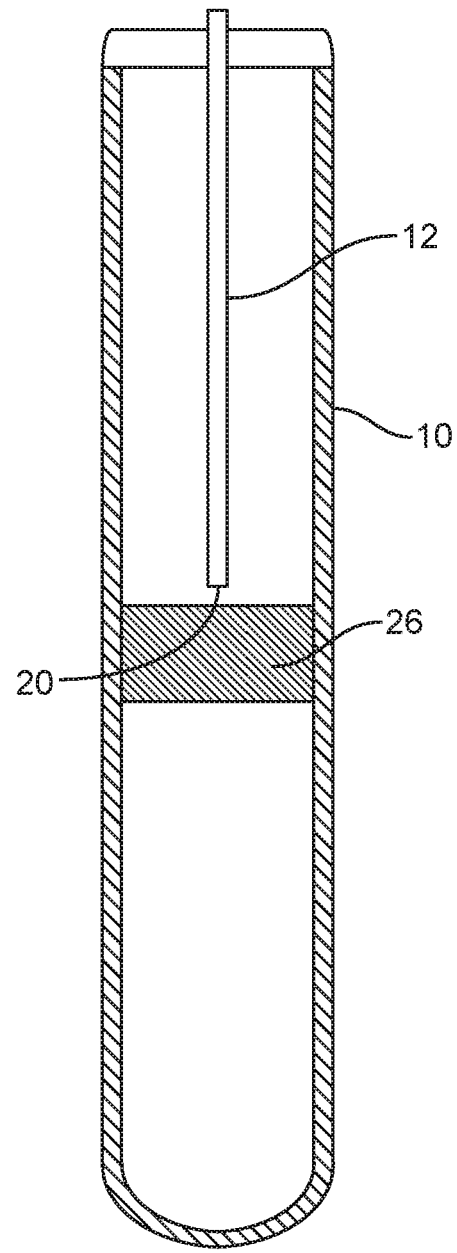

FIGS. 2B and 2C show partial cross-sectional side views of the tube 10 having alternative features to the matrix 24. The variation of FIG. 2B may incorporate a shelf 26 which functions as a stop for preventing the sedimented RBC layer from becoming disturbed. FIG. 2C shows another variation in which the matrix or foam 26 only partially fills the lower portion of the tube 10. For instance, the matrix or foam 26 may be formed into a disk or cylindrical shape positioned at approximately mid-height of the tube 10 just below the opening 20 of the access tube 12.

INVERSE PLUNGER

Figure 3:
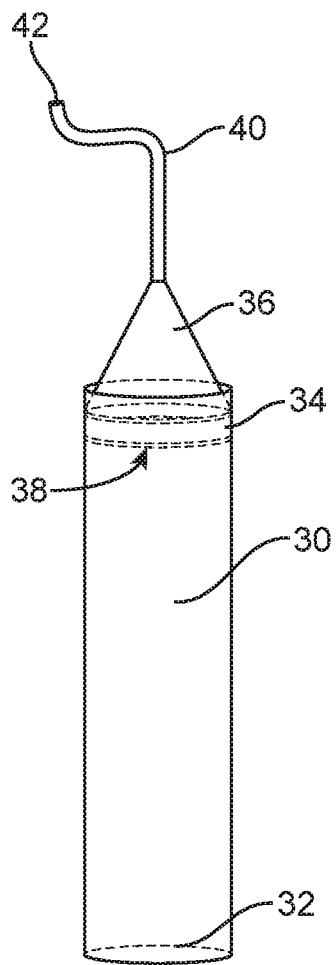
FIG. 3 shows a perspective view of another variation of a separation assembly having a funnel-shaped plunger assembly.

In yet another variation, FIG. 3 shows a perspective view of a cylindrical tube 30 having a closed floor 32 and a plunger 34 having a funnel 36 attached. A plunger opening 38 may be defined through the plunger 34 and a length of tubing 40 having an opening 42 may be connected to the apex of the funnel 36. In other variations, the plunger 34 and funnel 36 may be formed into a single integrated or uniform component having a single channel defined through the component between the plunger opening 38 and a funnel opening. As shown, rather than having a plunger pushed through the channel of the tube 30 from an end opposite of where the fractional layer is removed, the plunger 34 and funnel 36 may be used to remove the fractional layer from the same end of where the plunger 34 is actuated. In this manner, the plunger 34 is pushed down into the tube 30 and towards the floor 32 rather than from the bottom of the tube 30 away from the floor 32.

Figure 4A:
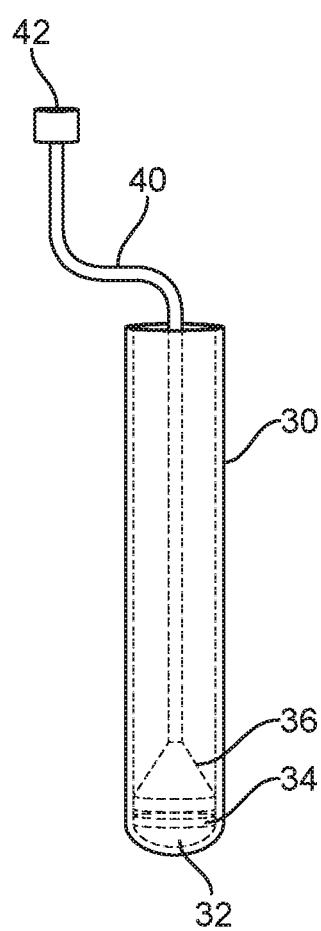
FIGS. 4A to 4G show an example of the separator assembly having the funnel-shaped-plunger used to separate and selectively collect the different blood components.
Figure 4B:
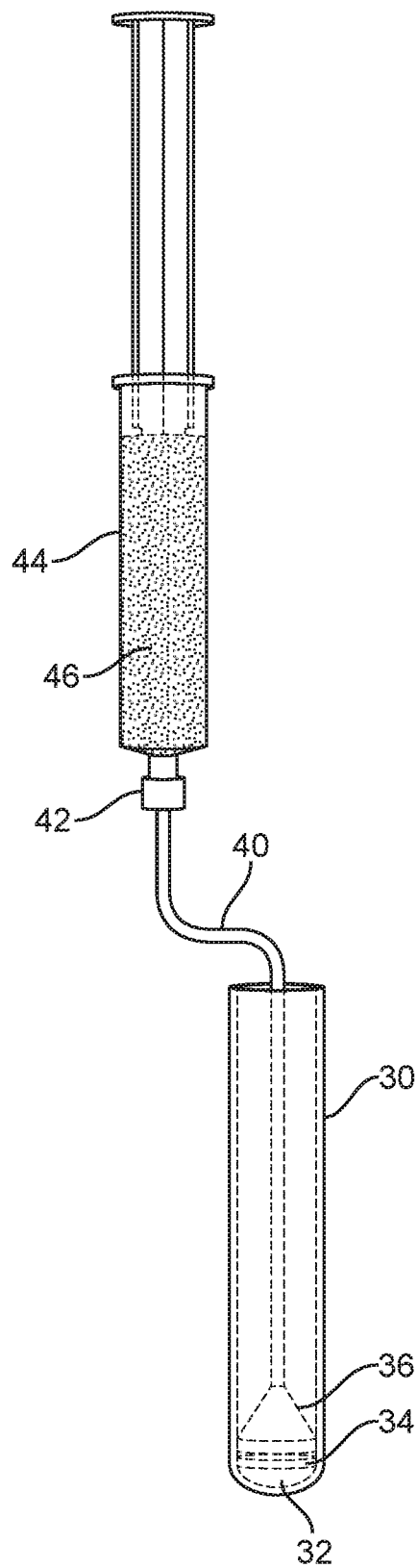
Figure 4C:
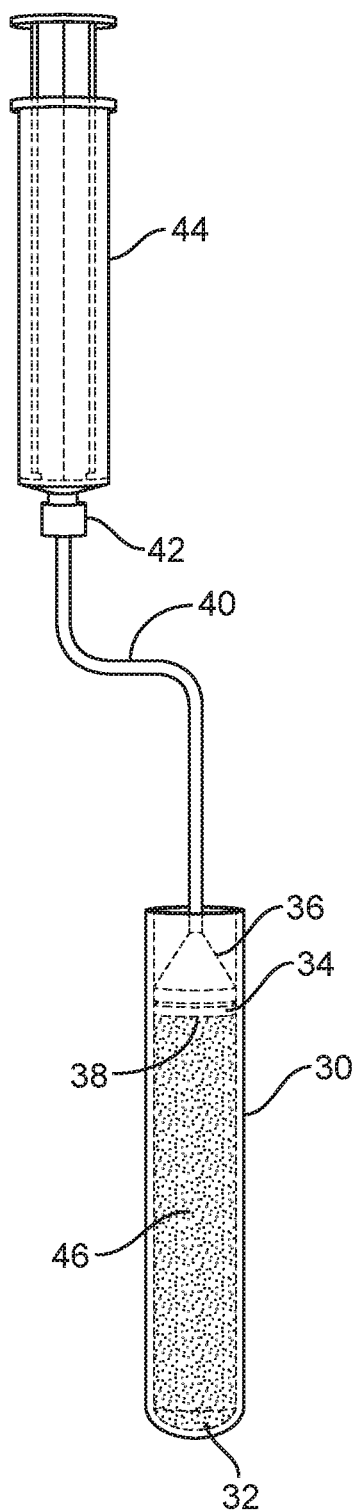

FIGS. 4A to 4G show one variation of a method for separating blood into its fractional layers and then withdrawing specific layers using the tube 30. As shown in FIG. 4A, the tube 30 may have the plunger 34 and attached funnel 36 initially positioned at the closed floor 32 of the tube 30. The tubing 40 may be seen extend from the funnel 36 through the tube 30 and terminating at the opening 42 positioned externally of the tube 30. A syringe 44 containing a volume of blood 46, e.g., anticoagulated blood, may be connected to the opening 42, as shown in FIG. 4B, and then injected through the tubing 40, into the funnel 36, through the plunger 34, and into the tube 30 which may force the plunger 34 and funnel 36 away from the floor 32 as the blood enters the tube 30, as shown in FIG. 4C.

Figure 4D:
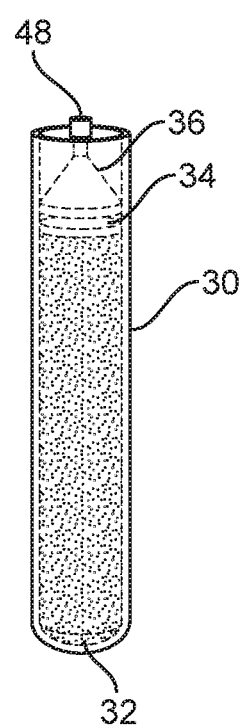
Figure 4E:
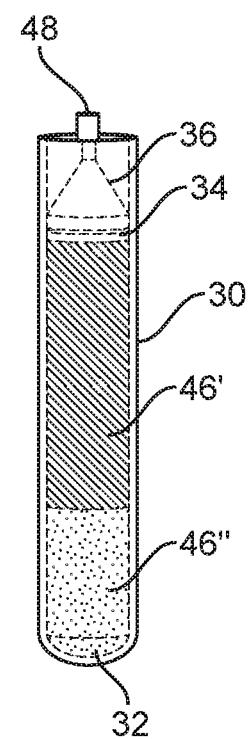

Once the tube 30 has been sufficiently filled with the blood 46, the tubing 40 may be detached from the top of the funnel 36 which may be secured with a cap or seal 48 in preparation for centrifugation, as shown in FIG. 4D, with the funnel 36 remaining in place upon the plunger 34. Once the tube 30 and blood 46 has been sufficiently centrifuged, the blood 46 may have fractionalized into its component layers, e.g., a first PRP layer 46' and a second RBC layer 46", as shown in FIG. 4E.

Figure 4F:
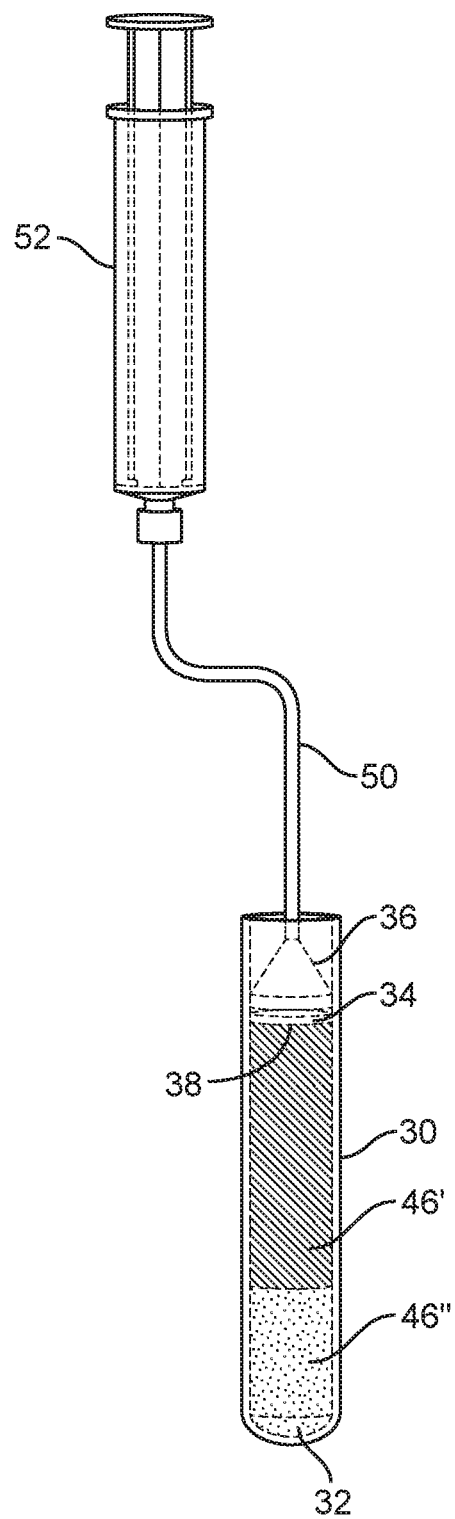
Figure 4G:
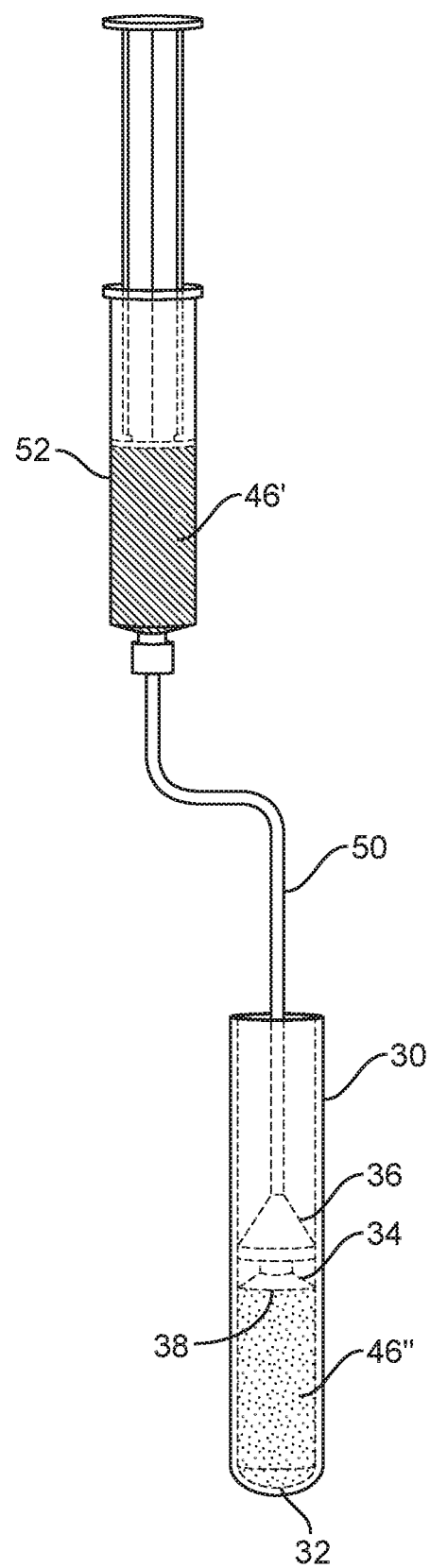

A tubing 50 connected to a withdrawal syringe 52 may be coupled to the funnel 36, as shown in FIG. 4F, and the syringe 52 may be used to draw the PRP layer 46' directly through the funnel 36 and into the syringe 52. Due to the vacuum drawn via the withdrawal syringe 52, the plunger 34 and funnel 36 may be forced to move further into the tube 30 and towards the floor 32 as the PRP layer 46' is removed from the tube 30, as shown in FIG. 4G.

During withdrawal, because the plunger 34 and funnel 36 are moving into the PRP layer 46' for collection, the platelets within the layer 46' are no longer dragged against the walls of the tubing 30. Moreover, because the PRP layer (buffy coat, RBC layer) remains undisturbed until contacted with the funnel 36, the yield on platelets and white blood cells are potentially improved while contamination from the RBC layer is potentially reduced.

For discussion purposes, a "hard spin" generally refers to the first spin in the double-centrifugation protocol for separating the red blood cells from the plasma while a "soft spin" generally refers to the second spin in the protocol which is used to further separate the platelets, white blood cells and few remaining red blood cells from the plasma. While not intended to be limiting, a "hard spin" may range, e.g., between 2000 to 4000×g over 2 to 20 minutes, while a "soft spin" may range, e.g., between 500 to 1000×g over 2 to 20 minutes.

In the case where the whole blood 46 has been subjected to a "soft spin", the fractionalized PRP layer may be withdrawn using the method described. In the case where the whole blood 46 has been subjected to a "hard spin", an additional fractional layer of platelet-poor plasma (PPP) may be formed atop of the PRP layer. The plunger 34 and funnel 36 may be partially translated through the tube 30 and towards the floor 32 to capture just the PPP layer, the PRP layer, or both, if desired. In the case where a buffy coat has been formed after a "hard spin", once the PRP layer has been withdrawn, a second withdrawal syringe may be connected and the buffy coat alone may then be withdrawn into the second withdrawal syringe.

The apparatus and methods disclosed above are not limited to the individual embodiments which are shown or described but may include combinations which incorporate individual features between the different variations. Modification of the above-described assemblies and methods for carrying out the invention, combinations between different variations as practicable, and variations of aspects of the invention that are obvious to those of skill in the art are intended to be within the scope of the claims.

What is claimed is:

1. A separation apparatus, comprising:
   a cylindrical tube defining an opening and a channel extending therethrough with a closed floor opposite of the opening;
   a plunger defining a plunger fluid opening and slidably positioned within the channel;
   a funnel attached upon the plunger and movable therewith, wherein the funnel narrows from a first width upon the plunger down to a second width which is smaller than the first width and which terminates in a funnel fluid opening extending away from the plunger and is in fluid communication with the plunger fluid opening; and
   a flexible tubing removably coupled to the funnel fluid opening,
   wherein the funnel and the plunger are configured to advance distally into the channel from a first position where the funnel fluid opening is positionable externally of the opening of the cylindrical tube to a second position where the funnel fluid opening is positionable within the channel when exposed to a vacuum formed below the funnel, the vacuum being formed through the funnel fluid opening when a fluid within the cylindrical tube is urged through the flexible tubing by entering through the first width and into contact with the funnel and to pass through the second width and into the funnel fluid opening.

2. The apparatus of claim 1 wherein the flexible tubing extends through the opening of the cylindrical tube when coupled to the funnel fluid opening.

3. The apparatus of claim 1 wherein the funnel is positioned upon a first side of the plunger in proximity to the opening of the cylindrical tube.

4. The apparatus of claim 1 further comprising a syringe fluidly coupled to the funnel fluid opening.

5. The apparatus of claim 1 wherein the funnel and the plunger form a single integrated component.

6. The apparatus of claim 1 further comprising a cap configured to seal the funnel fluid opening.

* * * * *